US008152592B1

(12) United States Patent
Lavigne

(10) Patent No.: US 8,152,592 B1
(45) Date of Patent: Apr. 10, 2012

(54) BREAST CREASE COMFORTER

(76) Inventor: Mary E Lavigne, Spokane, WA (US)

( * ) Notice: Subject to any disclaimer, the term of this patent is extended or adjusted under 35 U.S.C. 154(b) by 10 days.

(21) Appl. No.: 12/973,870

(22) Filed: Dec. 20, 2010

(51) Int. Cl.
A41C 3/00 (2006.01)

(52) U.S. Cl. ............................................. 450/79; 450/82

(58) Field of Classification Search ...................... 450/81, 450/36–38, 54–58, 1, 65, 66, 79, 82, 93, 450/92, 41, 45–49, 88; 2/67, 69, 73, 106, 2/105, 113–115; 66/171, 176, 177, 153, 66/172 E, 170, 169 R, 172 R, 173, 175
See application file for complete search history.

(56) References Cited

U.S. PATENT DOCUMENTS

| | | | |
|---|---|---|---|
| 3,772,899 A * | 11/1973 | Novi | 66/176 |
| 6,102,772 A * | 8/2000 | Fernandez | 450/1 |
| 6,406,353 B1 * | 6/2002 | Harper | 450/57 |
| 6,863,589 B2 * | 3/2005 | Cano | 450/65 |
| 7,077,719 B2 * | 7/2006 | Shiekman | 450/1 |
| 2005/0136795 A1 * | 6/2005 | Shiekman | 450/1 |

* cited by examiner

Primary Examiner — Gloria Hale
(74) Attorney, Agent, or Firm — Mark Farrell

(57) ABSTRACT

A breast crease comforter decreases pain and promotes healing during and after radiation therapy to the breast. The skin crease between the breast and the torso is typically exposed to daily friction, sheer, and moisture. When the breast is also compromised by radiation therapy, these various insults may combine to cause skin breakdown and excoriation, including resultant pain. The breast crease comforter intervenes between the underside of the breast and the torso to protect and pad this sensitive crease area when compromised by radiation therapy. The breast crease comforter may also be used to treat other conditions besides vulnerable skin resulting from radiation therapy to the breast or torso. The breast crease comforter may also be combined with the bottom of a conventional bra.

17 Claims, 4 Drawing Sheets

BREAST CREASE COMFORTER

TECHNICAL FIELD

The subject matter presented herein relates generally to medical accessories and more specifically to a breast crease comforter.

BACKGROUND

Radiation therapy for breast cancer and other conditions often leaves the breast tissue temporarily sensitive and the skin of the breast susceptible to physical friction. There may be no immediate side effects from individual radiation treatments given to the breast, but some patients may develop fleeting aches and pains in the breast. Patients usually develop a slight fatigue and some skin vulnerability that accumulates over the course of therapy. The most common side effect is the skin's reaction to radiation and to the chemotherapy that sometimes accompanies the radiation therapy. Most patients develop tenderness, dryness, reddening, and pruritis, or itching of the skin, after a few weeks. In other words, the radiation therapy may temporarily compromise the skin on the breast as well as the inner breast tissue itself, making these weaker than usual or at least more tender and sensitive to irritation and physical insult.

Following radiation therapy of the breast, patient care recommendations typically include cleanliness and preservation measures, such as keeping the skin clean and dry using warm water and neutral soap; avoiding extremes, such as high and low temperatures while bathing, trauma to the skin, sun exposure, shaving the treatment area with a sharp razor, perfumes, cosmetics, deodorants and so forth. Only prescribed or recommended creams and balms are allowed for daily maintenance.

Some patients develop a sunburn-like reaction with blistering and peeling of the skin. "Moist desquamation" can occur in the fold under the breast or in the fold between the breast and the arm, or in any area when the most radiation is given. A limited amount of moist desquamation may allow a person to continue treatment without interruption. When the degree is such that treatment must be interrupted, the skin usually heals enough within a week to allow radiation to be resumed. Skin side effects usually heal completely within a few weeks of completing radiation therapy. However, some skin reactions may take months to heal. Rarely, the skin is compromised (e.g., thinned or dried out) permanently.

There are also issues of slight swelling of the breast during radiation therapy. This can cause notable tenderness and other problems, but usually goes away within 6-12 months. The skin may darken during the course of radiation, similar to tanning from ultraviolet light, but in most cases this also fades gradually over 6-12 months. Most people receiving radiation suffer periodic aches and pains in the treated breast or the muscles surrounding the breast, even years after treatment has ended. The specific cause is unknown, but these pains are generally harmless. Very rarely, patients develop a more serious breakdown of the skin, fractures of the breastbone, or such severe pain in the breast that surgery is needed for treatment.

Radiation therapy given to the axillary lymph nodes can increase the risk of patients developing upper arm swelling from fluid retention ("lymphedema") following axillary dissection. Radiation to this area can cause pain and loss of strength in the hand and arm for years after treatment as well as numbness and tingling.

For sore skin in the breast area following radiation therapy, comfort padding measures tend to be homemade. Commercially available means to comfort and pad these delicate tissues during and after radiation therapy are needed.

SUMMARY

A breast crease comforter decreases pain and promotes healing during and after radiation therapy to the breast. The skin crease between the breast and the torso is typically exposed to daily friction, sheer, and moisture. When the breast is also compromised by radiation therapy, these various insults may combine to cause skin breakdown and excoriation, including resultant pain. The breast crease comforter intervenes between the underside of the breast and the torso to protect and pad this sensitive crease area when compromised by radiation therapy. The breast crease comforter may also be used to treat other conditions besides vulnerable skin resulting from radiation therapy to the breast or torso. The breast crease comforter may also be combined with the bottom of a conventional bra.

This summary section is not intended to give a full description of the breast crease comforter, or to provide a list of features and elements. A detailed description of example embodiments of the breast crease comforter follows.

DETAILED DESCRIPTION

Overview

Figure 1:
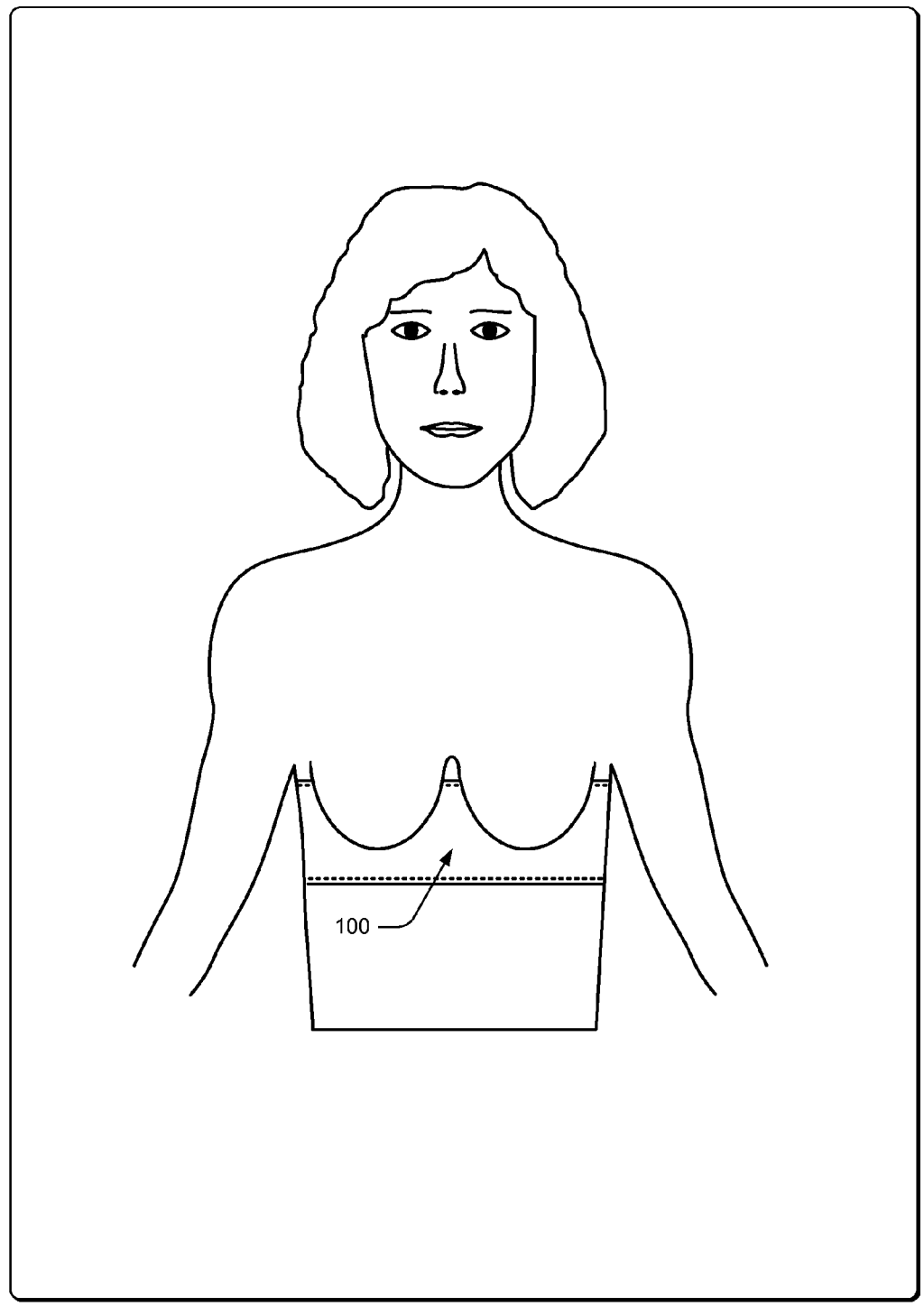
FIG. 1 is diagram of an example breast crease comforter for treating skin conditions caused by radiation therapy.
Figure 2:
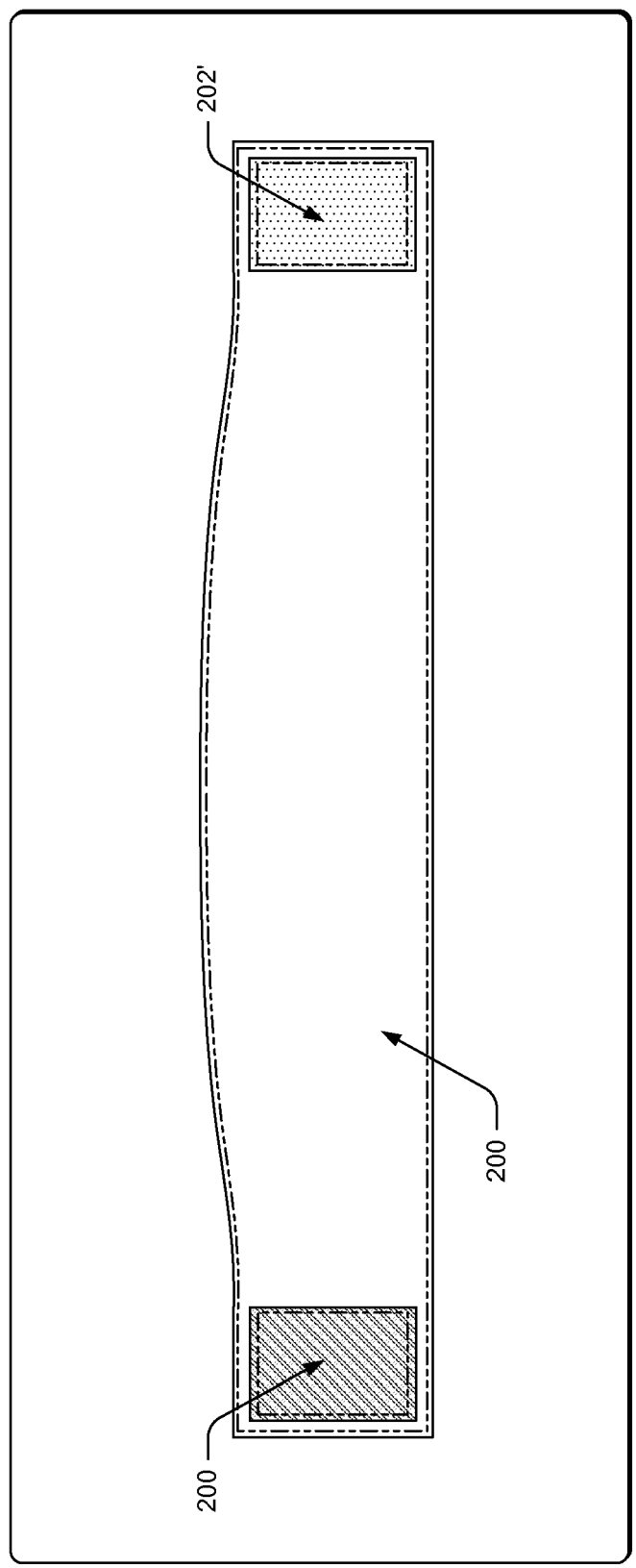
FIG. 2 is diagram of an example breast crease comforter and attachments.
Figure 3:
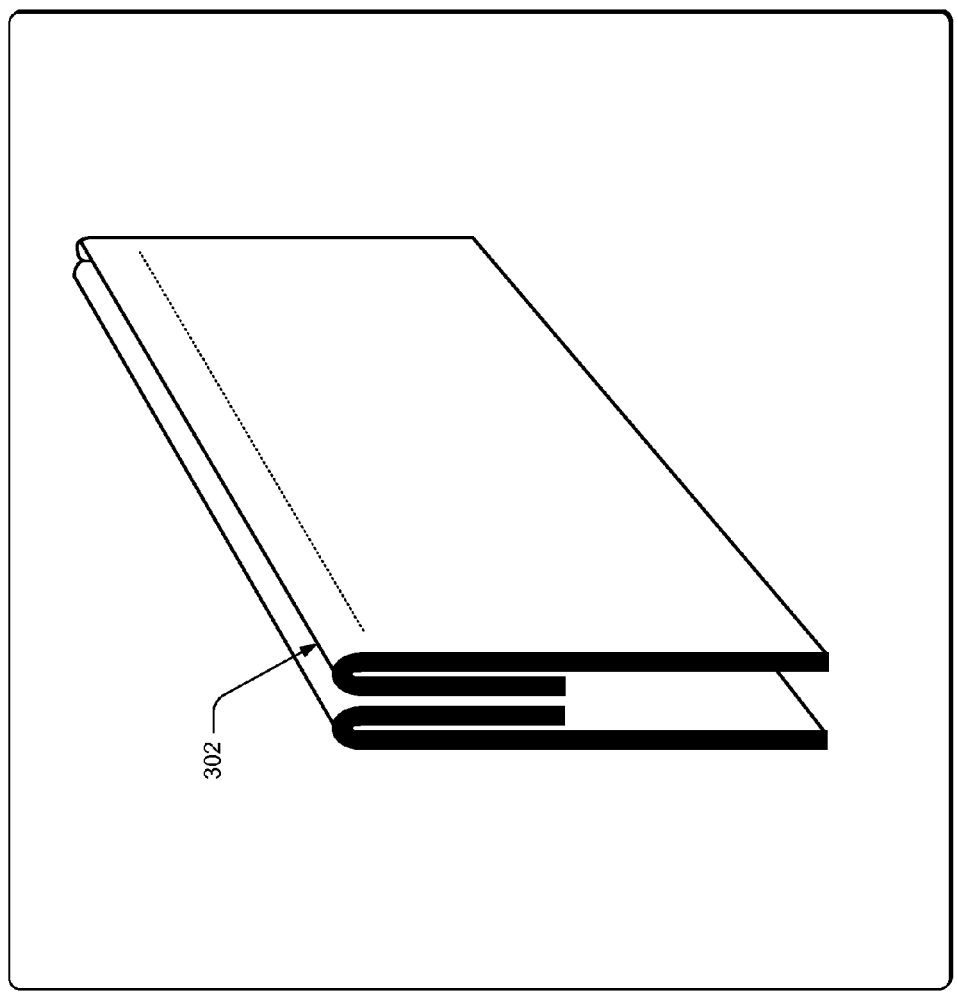
FIG. 3 is a diagram of an example seam technique for presenting a soft surface of the breast crease comforter to the skin.

As shown in FIG. 1, this disclosure describes a breast crease comforter 100 to decrease discomfort and promote healing during and after radiation therapy to the breast. Whereas a bra is designed to support the breasts through lift or containment, the breast crease comforter (hereinafter, "comforter" 100) intervenes between the underside of the breast and the torso to protect and pad this sensitive crease area when compromised by radiation therapy.

The skin crease between the breast and the torso is typically exposed to daily friction, sheer, and moisture. When the breast is also compromised by radiation therapy, these various insults may combine to cause skin breakdown and excoriation, including resultant pain. During radiation therapy, a bra typically presents a relatively irritating support structure to the sensitive crease area, just when the crease area needs soft padding and isolation from abrasion. The breast crease comforter 100 does not surround, lift, and support the breasts to a raised or contained position, rather the breast crease comforter 100 pads the crease where the underside of the breast meets the torso.

The breast crease comforter 100 may be used to treat other conditions besides vulnerable skin resulting from radiation therapy to the breast or torso. The breast crease comforter may also be combined with a conventional bra.

Construction

In one implementation, the breast crease comforter 100 is a band of soft material that fastens around the torso, with the top edge of the comforter under the bottom crease of the breast, i.e., at the crease where the underside of the breast meets the torso. The comforter 100 may be held in place by frictional forces between the comforter 100 and the skin and in some cases by the weight of the breasts on the comforter 100.

In another implementation, one side—the front—of the comforter 100 is soft, to pad the underside of the breast, while the other side of the comforter 100 has at least a slight tendency to adhere to skin, to hold the breast crease comforter 100 in place. In yet another implementation, the top half, including the top edge, of the breast crease comforter 100 is constructed with very soft material to comfort the breast crease, the skin on the underside of the breast, and the skin on the front of the torso, while the bottom half of the comforter is constructed of material selected to at least partially adhere to the skin to hold the comforter 100 in place.

Other means for holding the breast crease comforter 100 in place can be added depending on the dimensions of a particular comforter 100 and the dimensions and needs of the wearer. In one implementation, the back of the comforter 100 has rubber-like elements to assist holding the comforter 100 in place by adding friction between the comforter 100 and the skin. In another implementation, the breast crease comforter 100 has external adhesive tabs. A stretch material may be used to help keep the comforter 100 in place, but using a stretch material may defeat the purpose of providing soft, nonrestrictive padding and comfort.

In one implementation the breast crease comforter 100 consists of a soft fabric tube, and a flat stiffener inside the length of the soft fabric tube to form the soft fabric tube into a band 200. The soft fabric may be flannel, velvet, silk, etc., or combinations of materials to create a soft fabric. The soft fabric tube may be constructed of a single sheet of fabric or material folded over on itself, and the lengthwise edges fastened together (e.g., sewn). The two opposite edges may be joined with an inside seam 302 to maintain presentation of a soft surface to the user's skin.

The stiffener may be any flexible material, such as thick elastic, rubber, or another fabric or material that provides body and flatness to the comforter 100. A connector 202 (& 202'), such as a VELCRO connector, or other attachment means, such as snaps, clasps, buttons, zipper, etc., may be placed on each end of the soft fabric tube for adjustably connecting the ends of the soft fabric tube together, so that the band 200 forms a sized "ring" around a user's torso. The width of the flat stiffener can be adjusted to match an underside dimension of a user's breast.

The soft fabric tube may consist of a first type of fabric or material that makes up the torso side of the band 200 and a second type of fabric that makes up the breast side of the band 200. The fabrics can be selected so that the first fabric against the torso has a higher coefficient of friction than the second fabric that is to be placed against the breast. This second fabric is usually selected to be very soft. Thus, the first fabric or material may have adherent properties, to help keep the comforter 100 in place. For example, the first material may be composed of or include adherent areas that gently and reversibly adhere to the skin. Such adherent patches may have a rubber, silicone, or other adherent surface, or may be composed of moleskin, gore-tex, a dermal cover, a skin substitute material, such as SECOND SKIN (Spenco Medical Corporation, Waco, Tex.), etc., so that the band 200 "sticks" to the user's torso to some degree, while the other side of the band 200 remains soft. In one implementation the adherent parts of the comforter 100 are small patches that contact the user's back and/or sides, while leaving soft fabric on both sides of the band 200 where the band 200 contacts the underside of the breast, the crease, and the torso, all three of which may be sore or sensitive.

In one implementation, the ends of the comforter 100 allow access to the inside of the comforter when the comforter 100 is not in use: i.e., when the two ends of the band 200 are not attached to each other. The user can then place various accessories inside the comforter 100 to adjust the function and the dimensions of the comforter 100. In another implementation, the inside of the comforter 100 is accessible along its length, e.g., through a zipper or other separator.

In one implementation, the user can select a stiffener from a spectrum of stiffeners to adjust the width of the comforter 100 to suit the dimensions of the user's breasts. The user may also select the stiffness of the stiffener in this manner. The user may also insert pads of various thicknesses to adjust the thickness or softness of the overall comforter 100. The comforter 100 can accept other accessories that fit inside the soft fabric tube, such as a warming element that is either electric or microwave warmable; a vapor emitting element; a vibrating element; a cooling element; a drying element; etc. The inside space to accept these accessories may be the main inside space of the soft fabric tube, or may be a separate pocket.

Example Method

Figure 4:
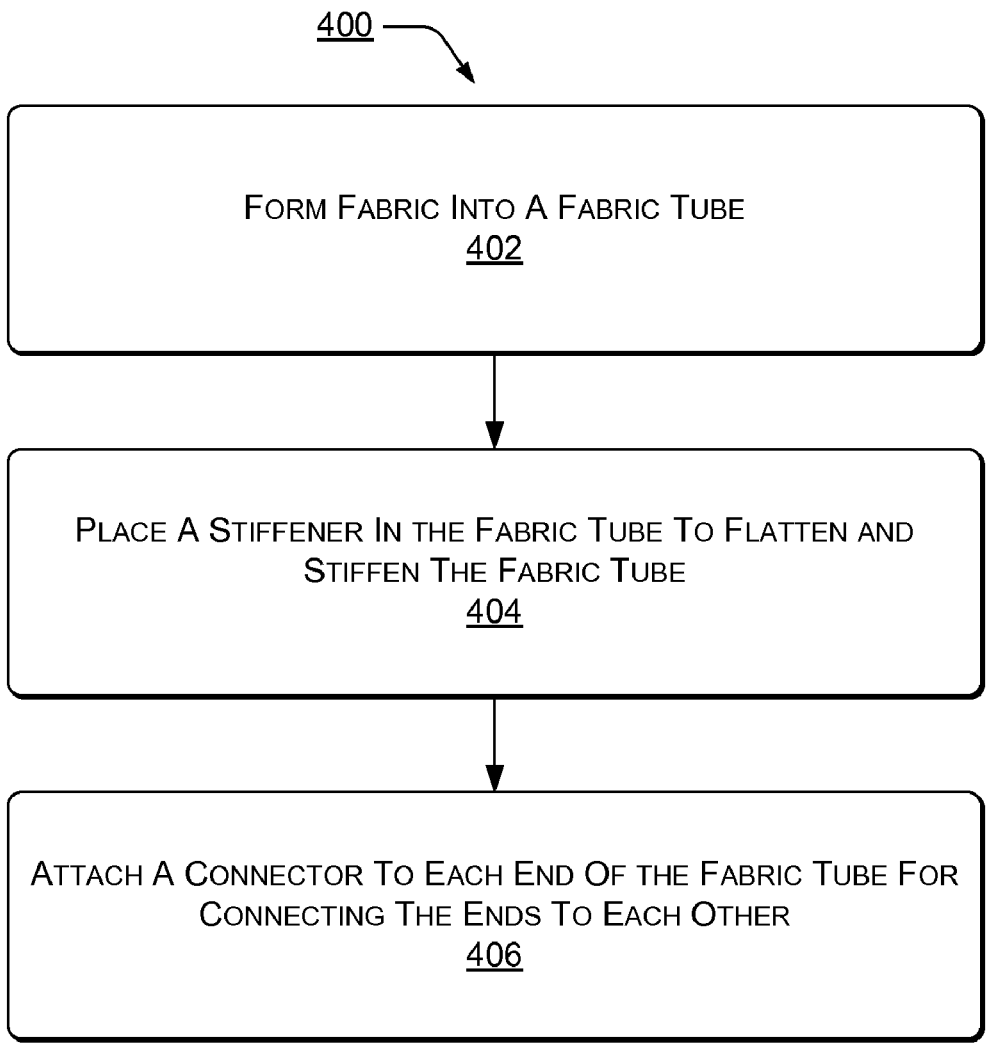
FIG. 4 is a flow diagram of an example method for constructing a breast crease comforter.

FIG. 4 shows an exemplary method 400 of constructing a breast crease comforter. In the flow diagram, the operations are summarized in individual blocks.

At block 402, fabric is formed into a fabric tube. At least part of the fabric tube is soft material intended to pad and comfort breast tissue that has been thinned, burned, or weakened by radiation therapy. Thus, the fabric tube can be made by taking a single piece of soft fabric, such as flannel, etc., and folding the piece over on itself. The two edges are then sewn or otherwise joined to each other. When the edges are sewn, an inside seam 302 may be used, so that soft fabric is always presented to the user's skin. In other implementations, the method may include fastening two types of fabric or material to each other to make the comforter. One of the fabrics is soft to pad the breast crease, while the other fabric has adherent properties to prevent the comforter from slipping out of place on the user's body. Alternatively, the method may include attaching adherent areas, e.g., patches, to the comforter to reversibly adhere to the skin in order to help keep the comforter in place on the body.

At block 404, a stiffener is placed in the fabric tube to flatten and stiffen the fabric tube. Placing the stiffener may include obtaining a width dimension corresponding to the underside of a breast, so that the comforter will be wide enough to pad the entire underside of the breast, if desired.

At block 406, a connector 202 is attached to each end of the fabric tube for connecting the ends to each other. The connectors may be VELCRO, a snap, a clasp, a button, a zipper, etc. When the connectors allow size adjustment of the comforter, then the comforter may be used with users of various sizes.

The comforter may also allow access to its interior, to customize the stiffness, width, thickness, and amount of padding provided. The inner space to be accessed may also be a pocket that is separate from the main interior of the comforter. The interior space can allow the user to vary stiffeners, width adjusters, thickness adjusters, or pads; and enable the user to place a warming element, a cooling element, a vibrating element, a vapor emitting element, a drying element, and so forth.

CONCLUSION

Although exemplary systems have been described in language specific to structural features and/or methodological acts, it is to be understood that the subject matter defined in the following claims is not necessarily limited to the specific features or acts described. Rather, the specific features and acts are disclosed as exemplary forms of implementing the claimed systems, methods, and structures.

The invention claimed is:

1. A breast crease comforter, comprising:
   a cupless fabric band having a first side and a second side and configured to be worn around a human torso with only a top edge of the cupless fabric band contacting an underside crease of a breast of a patient after radiation therapy;
   a reversibly adherent surface on the first side for contacting and gently gripping a skin area circumferent around a torso of the patient;
   a soft padded surface on the second side for cushioning an underside of a breast of the patient;
   a connector on each end of the cupless fabric band for adjustably connecting the ends of the cupless fabric band together around the torso;
   wherein the cupless fabric band comprises a single piece of fabric folded over on itself with two opposite edges of the single piece of fabric joined to make a fabric tube;
   an opening and closing means attached to at least one part of the fabric tube for enabling access to an inner space of the fabric tube; and
   wherein the inner space comprises an additional pocket separate from the fabric tube.

2. The breast crease comforter of claim 1, wherein the cupless fabric band comprises a fabric tube with a flexible stiffener; and
   wherein a width of the flexible stiffener is adjustable to match an underside dimension of the breast.

3. The breast crease comforter of claim 1, wherein the cupless fabric band comprises a first fabric on the first side of the cupless fabric band and a second fabric on the second side of the cupless fabric band.

4. The breast crease comforter of claim 3, wherein the second fabric comprises one of flannel, velvet, or silk.

5. The breast crease comforter of claim 2, wherein the flexible stiffener comprises an elastic band.

6. The breast crease comforter of claim 1, wherein the reversibly adherent surface further comprises at least one adherent patch.

7. The breast crease comforter of claim 1, wherein the reversibly adherent surface further comprises at least one adhesive tab.

8. The breast crease comforter of claim 1, wherein the connector comprises one of a hook and loop fastener, a snap, a clasp, a button, or a zipper.

9. The breast crease comforter of claim 1, wherein the cupless fabric band comprises a single piece of fabric with two opposite edges joined to make a tube;
   wherein the two opposite edges are joined with an inside seam to maintain a presentation of a soft surface to the user's skin.

10. The breast crease comforter of claim 9, wherein ends of the breast crease comforter enable access to an inside space of the tube; and
    wherein the inside space is capable of containing one of a stiffener, a pad, a warming element, a cooling element, a vibrating element, a vapor emitting element, or a drying element.

11. The breast crease comforter of claim 10, wherein the inside space contains a pocket attached to an inside surface of the tube but separate from the inside space.

12. A method of constructing a breast crease comforter, comprising:
    forming a fabric into a cupless fabric band having a first side and a second side;
    creating a reversibly adherent surface on the first side for contacting and gently gripping a skin area circumferent around a torso of a patient after radiation therapy;
    creating a soft padded surface on the second side for cushioning an underside of a breast of the patient;
    attaching connectors to each end of the cupless fabric band for connecting the ends of the fabric tube to each other around the torso with only an upper edge of the cupless fabric band contacting an underside crease of a breast of the patient;
    wherein forming the cupless fabric band comprises folding a single piece of fabric over on itself; and
    further comprising joining two opposite edges of the single piece of fabric to make a fabric tube, attaching an opening and closing means to at least one part of the fabric tube for enabling access to an inner space of the fabric tube, wherein the inner space comprises an additional pocket separate from the fabric tube.

13. The method of claim 12, further comprising obtaining a depth dimension corresponding to the underside of a breast; and
    forming the cupless fabric band to equal the depth dimension.

14. The method of claim 12, wherein forming the cupless fabric band comprises fastening a first fabric for the first side to a second fabric for the second side.

15. The method of claim 12, further comprising attaching at least one adherent patch to the cupless fabric band to make the reversibly adherent surface.

16. The method of claim 12, further comprising attaching at least one adhesive tab to the cupless fabric band to make the reversibly adherent surface.

17. The method of claim 12, further comprising inserting an accessory into the inner space, wherein the accessory is one of a stiffener, a pad, a warming element, a cooling element, a vibrating element, a vapor emitting element, or a drying element.

* * * * *